United States Patent [19]
Fuisz

[11] Patent Number: 5,034,421
[45] Date of Patent: Jul. 23, 1991

[54] MODERATED SPUN FIBROUS SYSTEM AND METHOD OF MANUFACTURE

[75] Inventor: Richard C. Fuisz, Washington, D.C.

[73] Assignee: Fuisz Pharmaceutical Ltd., Washington, D.C.

[21] Appl. No.: 325,643

[22] Filed: Mar. 20, 1989

Related U.S. Application Data

[63] Continuation-in-part of Ser. No. 283,742, Dec. 13, 1988, and a continuation-in-part of Ser. No. 169,838, Mar. 18, 1988, Pat. No. 4,855,326, and a continuation-in-part of Ser. No. 169,914, Mar. 18, 1988, Pat. No. 4,873,085, said Ser. No. 283,742, is a continuation-in-part of Ser. No. 169,838, Mar. 18, 1988, Pat. No. 4,855,326, which is a continuation-in-part of Ser. No. 40,371, Apr. 20, 1987, abandoned, said Ser. No. 169,914, is a continuation-in-part of Ser. No. 40,371, Apr. 20, 1987, abandoned.

[51] Int. Cl.$^5$ ............... A61K 9/16; A61K 9/20; A61K 9/68; A61K 9/70
[52] U.S. Cl. ................... 514/772; 514/777; 514/781; 424/410; 424/439; 424/440; 424/443; 426/658; 426/517; 127/24
[58] Field of Search ............ 514/772, 777, 781, 974; 424/400, 439, 440, 443; 425/9; 426/658, 660, 517; 206/569; 127/24

[56] References Cited

U.S. PATENT DOCUMENTS 4,855,326  8/1989  Fuisz ................................. 514/777
4,873,085  10/1989  Fuisz ............................... 514/777

Primary Examiner—Nathan M. Nutter
Attorney, Agent, or Firm—Brooks Haidt Haffner & Delahunty

[57] ABSTRACT

A spun product from a combination of a saccharide and a hydrophobic ingredient is hydrophilic with low concentrations of such ingredient but becomes increasingly hydrophobic as the concentration of the hydrophobic ingredient is increased, although the end product nevertheless acts hydrophilically when the water temperature is elevated. Larger ratios of hydrophobic substance-to-saccharide yields a spun fibrous product that has increased stability. Similar stabilization can be attained by adding either beeswax or a petrolatum to the saccharide either in the presence of or absence of a separate active ingredient. Examples are given for masking the taste of unpalatable medicaments or other ingestible substances. Delayed release burn or wound dressings are also described. Control with beeswax can also provide a time release tablet or the like when swallowed.

51 Claims, No Drawings

MODERATED SPUN FIBROUS SYSTEM AND METHOD OF MANUFACTURE

BACKGROUND OF THE INVENTION

This application is a continuation-in-part of application Ser. No. 07/283,742, filed Dec. 13, 1988, pending which is a continuation-in-part of application Ser. No. 07/169,838, filed Mar. 18, 1988 U.S. Pat. No. 4,855,326, which is a continuation-in-part of application Ser. No. 07/040,371, filed Apr. 20, 1987 abandoned. The present application is also a continuation-in-part of said application Ser. No. 07/169,838 U.S. Pat. No. 4,855,326, and of application Ser. No. 07/169,914, filed Mar. 18, 1988 U.S. Pat. No. 4,873,085, which is another continuation-in-part of application Ser. No. 07/040,371 abandoned.

In the prior applications preceeding Ser. No. 07/283,742, pending various substances having pharmacological and or cosmetic properties were combined with a sugar and spun into fibers to produce a readily water-soluble product. The various examples enumerated in those applications involved the use of water soluble medicaments and cosmetic substances and were directed to enhancing the solubility rate of the different substances. As an outgrowth of experimentation with a varied catalog of substances it was discovered that spinning a substance with a sugar can alter the medium in which a particular substance can either dissolve or become dispersed, the latter while forming a colloid or colloidal-like dispersion. Whether or not the dispersions described in the various applications represent true colloidal dispersions or only pseudo-colloidal dispersions, has yet to be determined, although all the evidence seems to favor the conclusion that a true colloid is formed. In any event, when the spun sugar products described in the applications are added to water, the product disperses autogenously throughout the water and remains dispersed. In most instances one observes a general cloudiness associated with a colloidal suspension. But this is not always the case. Several other novel phenomena have been observed also.

The disclosure in application Ser. No. 07/283,742 pending deals with oleaginous substances such as vegetable oil, baby oil, olive oil, margarine, lanolin, cocoa butter and the like, and how their lack of affinity for water is altered by mixing the oleaginous substance with sugar and melt spinning the mixture in a cotton candy spinning machine or the equivalent. As so modified the products disperse autogenously in water forming a colloidal or colloidal-like dispersion. Such modification enables such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify.

However, there are occasions when rapid dissolution or dispersion is to be avoided, and it has now been discovered that the rate at which the spun fibers disperse in water can be controlled. Also discovered are the methods necessary to accomplish such control.

SUMMARY OF THE PRESENT INVENTION

It is, therefore, an object of the present invention to provide a method for producing a medicament-bearing spun fibrous product having a predetermined release pattern.

It is another object of the present invention to provide a method for stabilizing spun saccharide.

Yet another object of the present invention is to provide a pharmaceutic dosage unit of compacted spun fibers which is stabilized to reduce the rate at which the spun fibers enter into a dispersed state when added to water.

Another object of the present invention is to provide a dermatologically effective topical delivery system from spun fibers whose dispersal rate in water has been reduced for effective application as a burn dressing or the like.

Still another object of the present invention is to provide a method for tempering the release time of the various constituents of a product containing spun fibers for oral consumption.

Other objects will occur to those skilled in the subject art after reading the present disclosure.

In accordance with one aspect of the present invention there is provided a method for preparing a medicament-bearing product having a predetermined release pattern comprising producing a mass of medicament-bearing spun fibers by melt spinning a composition containing said medicament and at least one saccharide where the content of said composition has been selected such that said mass of spun fibers when added to water at normal room temperature appears to be hydrophobic but disperses to form a colloidal or colloidal-like dispersion when the temperature of said water is elevated sufficiently above normal room temperature.

In accordance with another aspect of the present invention there is provided a method of stabilizing spun saccharide which comprises in combination the steps of combining with at least one saccharide capable of being spun into fibers that are readily water-soluble a quantity of a substance selected from the group consisting of petrolatum, beeswax and combinations thereof, and thereafter processing said substance and saccharide combination using a floss producing machine to yield a mass of spun fibers.

In accordance with a further aspect of the present invention there is provided a pharmaceutic dosage unit comprising compacted spun fibers of a spinnable, readily watersoluble material, an effective amount of a medicament, and an ingredient other than said medicament and said material which ingredient stabilizes said spun fibers and reduces the rate at which said spun fibers enter into a dispersed state when added to water.

In accordance with yet another aspect of the present invention there is provided a dermatologically effective topical delivery system comprising a mass of spun fibers containing a saccharide and a dermatologically effective active ingredient where said mass of fibers when added to water at normal room temperature disperse at a slower rate than spun fibers of said saccharide alone.

In accordance with a still further aspect of the present invention there is provided a product for consumption by introduction through the oral cavity where at least one of the ingredients of the product is noticeably unpalatable if introduced alone, said product comprising compacted spun fibers of a spinnable, readily water-soluble material that is both palatable and able, when simultaneously present in the oral cavity with said unpalatable ingredient, to mask said unpalatableness, a quantity of an unpalatable ingredient having a slower rate of dissipation in the oral cavity than said readily soluble material when only the two are present, and a moderator substance for retarding solubilization of said readily soluble material to cause said readily soluble material to remain in the oral cavity at least as long as said unpalatable ingredient.

The invention will be better understood after reading the following detailed description of the presently preferred embodiments thereof.

DETAILED DESCRIPTION OF THE PRESENTLY PREFERRED EMBODIMENTS

Co-pending application Ser. No. 07/169,838 describes methods for combining a medicament with any one or more of the water soluble melt spinnable sugars and spinning the combination to produce a readily soluble floss form of the medicament. The disclosure of such application is incorporated herein by reference.

Co-pending application Ser. No. 07/283,742 discloses that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. All of the examples included in said application Ser. No. 07/283,742 assumed addition of the fibrous product to water at normal room temperature. The disclosure of such application is incorporated herein by reference.

Co-pending application Ser. No. 07/169,914 discloses methods for combining a cosmetologically effective substance with any one or more of the water soluble melt spinnable sugars and spinning the combination to produce a readily soluble floss form of the cosmetologic substance. The disclosure of such application is incorporated herein by reference.

As a result of further experimentation it has now been discovered that if the ratio of oleaginous material to sugar (saccharide) exceeds a certain value, the precise crossover point being a function of the particular oleaginous material and sugar, the floss product will no longer disperse rapidly in water at normal room temperature. However, rapid dispersal as an apparent colloidal system does take place at elevated water temperatures. It has also been discovered that similar results can be obtained by admixing with the sugar, with or without other ingredients, suitable quantities of certain semi-solid substances that individually are practically insoluble in water, such as beeswax or petrolatum. In general, the fibrous products produced by the examples to be described give the appearance when added to water at normal room temperature of being hydrophobic. Compacted quantities of the fibrous product actually float on the surface of the water. But as soon as the water temperature is raised above some critical level for the particular fiber product, the fibrous product disperses rapidly throughout the body of water forming what appears to be a colloidal dispersion. The invention can best be described and understood from a consideration of a number of examples.

For the following examples the floss spinning machine used was: Econo floss Model 3017 manufactured by Gold Medal Products Co. of Cincinnati, Ohio. Unless otherwise stated, reference to sucrose in the examples is to "Gold Medal" flossugar, Jolly Berry flavor. Unless otherwise indicated, the temperature of the grid in the spinning machine was about 180° F. (82.2° C.) while the operating speed was about 3800 R.P.M.

EXAMPLE I

A quantity of sucrose was mixed with a quantity of Crisco 100% pure vegetable oil in the ratio of 3:1, respectively, by volume and stirred to produce a generally uniform blend. The mixture was spun with the floss spinning machine while additional vegetable oil was poured into the hub of the spinner. The resultant floss was very tough and very oily.

It should be mentioned that where the ingredient mixed with the sugar is naturally liquid some liquid tends to be ejected from the mixture as a result of the centrifugal forces developed by the spinning head such that oil, for example, is seen to deposit on the walls of the machine at start-up tending to reduce the oil content of the final fibrous product. Consequently, when working with liquids it may become necessary to add additional liquid to the spinning hub to maintain the desired concentration.

Next, a beaker containing water at normal room temperature was supplied with ⅛ cup of the produced vegetable oil floss. After 8 hours at least 50% of the original floss was still intact.

When the same floss was added to water at about 180° F. (82.2° C.) it dispersed rapidly very much like the floss with lesser oil content did in room temperature water as explained in application Ser. No. 07/283,742 pending.

EXAMPLE II

A broad spectrum antibiotic ointment marketed by Burroughs Wellcome Co. of North Carolina under the trademark "NEOSPORIN" was blended with sucrose in the ratio of 1 teaspoon ointment to 4 teaspoons sucrose. The ointment was worked into the sucrose with a spatula until an even mixture was obtained. The mixture was then spun with the floss machine. A rich floss was produced, not greasy and having the feel resembling that of a mass of polyester fiber. A quantity of this floss was compacted slightly into a body about ½ inch thick and about 1 inch in diameter. When placed in a vessel containing water at normal room temperature it remained intact floating high on the surface of the water. It took approximately 4 hours to disperse completely.

A similar quantity was placed on a sponge that was saturated with water and the fibers now took about 6 hours to disperse.

EXAMPLE III

Two teaspoons of "Vaseline" petroleum jelly manufactured by Cheesborough Ponds was mixed with 5 teaspoons of sucrose and processed into fibers in the same manner as in Example II. The resulting floss was very rich and more polyester like than in Example II. When placed in water as in Example II, the dispersion rate was even slower, taking approximately 6 hours. On the wet sponge after 8 hours there still remained a thin spread of fibers about 1/16 inch thick, having started with a sample approximately 1 inch in diameter and ½ inch thick.

EXAMPLE IV

Example III was repeated with the exception that the petroleum jelly was first melted in a container over a burner before being mixed with the sucrose. The results were exactly the same as those obtained in Example III.

EXAMPLE V

One teaspoon of "BEN GAY" ointment manufactured by Pfizer, Inc. was mixed with 4 teaspoons of sucrose. It was mixed, spun and tested the same as in Example II. In a vessel of room temperature water it floated initially completing dispersion in about 2 hours. On a wet sponge it took about 4 hours to disperse.

Comparing the results of Examples II to V one can observe a common thread. The "NEOSPORIN" ointment of Example II consists of Polymyxin B Sulfate, bacitracin zinc, and neomycin sulfate in a base consisting of special white petrolatum. In Example III the additive was a petrolatum. Petrolatum, as well as the vegetable oil in Example I, is practically insoluble in water. Similarly, in Example V the carrier is a blend of lanolin, microcrystaline wax, and synthetic beeswax where the lanolin and beeswax, and probably the microcrystaline wax, are practically insoluble in water.

With the concentrations used in the examples set forth in copending application Ser. No. 07/283,742, the oleaginous substances, all practically insoluble in water, were bound somehow within the sugar in a way to behave hydrophilically and disperse. For the present, no attempt is being made to theorize on an explanation of the phenomena observed in the Examples presented here. The observable condition is that with the concentrations or compositions used herein the flosses tend not to disperse dramatically in water at normal room temperature although they eventually disperse in such water. The rate of dispersal in water, however, increases with increasing water temperature.

EXAMPLE VI

Following the procedure of Example II, a series of flosses were prepared using lard and sucrose. Samples of the floss were then added to water both at room temperature and at 200° F. with the results presented in table I.

TABLE I

| Ingredient | Ratio to Sucrose | Water Temp. | REMARKS |
|---|---|---|---|
| Lard | 1:5 | rm. tmp. | Immediate rapid dispersal |
| Lard | 1:5 | 200° F. | Immediate rapid dispersal |
| Lard | 1:4 | rm. temp. | Floss visible after 4 hrs. |
| Lard | 1:4 | 200° F. | Immediate rapid dispersal |
| Lard | 1:3 | rm. temp. | Floss visible after 7 hrs. |
| Lard | 1:3 | 200° F. | Immediate rapid dispersal |
| Lard | 1:2 | rm. temp. | Floss visible after 10 hrs. |
| Lard | 1:2 | 200° F. | Immediate rapid dispersal |

With each of the tests recorded in table I, dispersal of the floss in room temperature water could be accelerated by stirring. However, stirring was unnecessary with 200° F. water.

EXAMPLE VII

Samples of floss produced in Examples II, III and V were also tested in both room temperature water and water at about 200° F. with results much the same as with the lard in Example VI. That is, floss that did not disperse immediately in room temperature water did disperse immediately in water at about 200° F.

EXAMPLE VIII

A 1/2 oz. piece of pure white pharmaceutical grade beeswax was placed in an ordinary coffee grinder and ground into small granules approximating that of the sucrose. One half teaspoon of beeswax granules was mixed with 8 teaspoons of sucrose (ratio of 1:16) and stirred thoroughly for several minutes. The mixture was spun producing an excellent floss with a slight odor of beeswax. When added to normal room temperature water it floated, but in water at about 180° F. it immediately dispersed with the appearance of being colloidal.

A sample was placed in the mouth of the experimenter on the tongue with the observation that the material seems to hesitate for about 1 to 2 secs. and then dissipates rapidly although slightly less rapidly than pure sugar floss without beeswax. No unpleasant taste was experienced from the beeswax.

EXAMPLE IX

The procedure of Example VIII was repeated with the ratio of beeswax to sucrose increased to 1:12. This time the delay on the tongue was about 3 secs. with it taking an additional 2 secs. to disperse entirely.

EXAMPLE X

Samples of the floss produced in Examples VIII and IX were subjected to a humid atmosphere by placing them in an open dish within 3 feet of a continually running hot shower in a bathroom for about 60 minutes without any noticeable degradation.

EXAMPLE XI

Another broad based antibiotic ointment, "LANABIOTIC" by Combe, Inc. of White Plains, N.Y., consisting of Bacitracin, Neomycin sulphate, Polymyxin B, and lidocaine (a pain killer) in a base of Lanolin, Mineral Oil, and Petrolatum, was mixed with sucrose in the ratio of 1:4 and spun. The resulting floss was excellent in texture and feel. When added to room temperature water it floated, but in hot water at about 180° F. the floss immediately and rapidly dispersed to form a colloidal or colloidal-like dispersion.

EXAMPLE XII

In this example "LANACORT", a topical delivery system consisting of hydrocortisone acetate 0.5% in cetyl alcohol, sorbitol, methyl paraben, aloe vera gel., propyl paraben, fragrance and zinc pyrithione was mixed with sucrose in the ratio of 1:4 and spun. When this fiber product was added to water it went into solution with no apparent evidence of the formation of a colloidal dispersion.

EXAMPLE XIII

Example XII was repeated, except that 2 parts "Vaseline" petroleum jelly was added to the mixture and blended before spinning. The resulting floss floated on room temperature water, but formed a colloidal or colloidal-like dispersion substantially immediately upon introduction to hot water at a temperature of 180° F.

EXAMPLE XIV

For this example 1 part "Maalox" Antacid Oral Suspension, produced by William H. Rorer, Inc. of Fort Washington, Pa., was stirred in a vessel with 6 parts sucrose. The mixture was then spun producing a whitish pink floss. "Maalox" antacid suspension is a balanced combination of magnesium and aluminum hydroxides. When a quantity of this floss was added to water in a vessel, the floss immediately dispersed to form a colloidal or colloidal-like dispersion. When a wad of the floss about the size of a quarter and ¼ inch thick was placed in the mouth of the experimenter on the tongue, it dispersed and dissipated immediately leaving a noticeable "Maalox" antacid aftertaste.

EXAMPLE XV

Example XIV was repeated, but this time ¼ tsp. ground beeswax USP was blended into the mixture before spinning. The floss again had a whitish pink color. However, when added to room temperature water, the floss floated on the surface. When a wad was placed in the mouth of the experimenter on the tongue, the material sat on the tongue for about 2 secs. and then was gone within an additional 3 secs. This time no aftertaste of the "Maalox" antacid could be detected. Instead, all that could be tasted was the sucrose. The taste test was repeated four additional times with substantially the same results.

EXAMPLE XVI

Tablets of Apple Pectin by Kal of Woodland Hills, Calif. were crushed and 1 teaspoon of the crushed ingredients was placed in a vessel along with 6 teaspoons of sucrose and 1 teaspoon of "Vaseline" petroleum jelly. The combination was stirred with a spoon until well blended, then spun. Excellent floss was produced. When a wad of floss ½ inch thick and 1 inch in diameter was placed in water at room temperature, the wad took 3 to 4 hours to dissipate completely. The petroleum jelly and pectin appeared to collect on the surface of the water as the sugar associated with the particles tended to dissolve in the water.

The foregoing examples are presented to provide the reader with a basic understanding of the principles of the invention. Those skilled in the relevant art will immediately appreciate the manifold uses to which the principles can be applied. A few of these will now be discussed.

In the treatment of severe burns it is well known that petroleum jelly is efficacious when applied topically. However, the burnt areas of the individual are so tender and sensitive that strong narcotic analgesics such as morphine are often required before the petroleum jelly can be applied. With the present invention the need for analgesics is greatly reduced if not eliminated. A floss produced, for example, from petroleum jelly as in Example III, with the addition of antibiotics and/or topical pain killers as in Example XI can be applied to the burn area. Because the floss is extremely light, a large wad or poultice-like mass can be placed on the burn area with minimum pressure and without abrading or rubbing action. Initially, the floss mass is dry, but as the burnt flesh releases sera, the medication in the floss is gradually released. Petroleum jelly, or at least the oils therefrom, is gradually deposited out upon the burnt tissue. The sugar, in and of itself having therapeutic value as a burn dressing, is also released, along with any antibiotics and/or topical pain killers.

If a petrolatum is the active ingredient, the release time can be determined by selecting the ratio of petrolatum to saccharide in the floss. If the active ingredient or medicament includes a quantity of petrolatum, controlling the ratio relative to saccharide will determine the release time. On the other hand, if the active ingredient does not contain an oleaginous constituent, release time can be controlled by adding a suitable quantity of either beeswax or petrolatum. Therefore, starting with one or more of the saccharides as a carrier, various medicaments can be co-spun with the release time or pattern predetermined by either controlling the ratio of saccharide to active ingredient or by a suitable release controlling additive or by a combination of both. Since various petrolatums are presently compounded with topical medicaments, the present invention provides a versatile delivery system where the otherwise hydrophobic composition is rendered dispersable in water at a controlled rate.

The ointment mentioned in Example II has application to burn dressing as well as the pectin used in Example XVI. An excellent burn dressing can be produced following the procedure set forth in these examples.

Where sustained release is desired, if the product is to be used externally, a suitable quantity of petrolatum can be included with the saccharide and active ingredient unless the active ingredient itself contains a petrolatum, in which case the saccharide-to-ingredient ratio is suitably selected. Where the product is for internal use, beeswax can be added in suitable proportion. Here, the beeswax delays the release of the saccharide, either for matching its release time to that of the active ingredient or for producing an otherwise delayed release medication.

Example X reveals another feature of the present invention. Where stabilization of the saccharide floss to humidity attack is required, a suitable quantity of beeswax can be added to the mixture that is spun.

Examples VIII, IX, XIV and XV demonstrate another feature, namely the ability to mask the taste of a distasteful or unpalatable medicament or the like. Generally, the medicament or active ingredient is not absorbed as rapidly in the mouth as the saccharide. By adding a suitable quantity of beeswax, the release and absorbtion of the saccharide can be slowed to match that of the active ingredient whereby any objectionable taste is successfully masked.

However, the control afforded by beeswax goes way beyond mere masking of taste. Where delayed action release of medication is desired, the medicament can be combined with one or more saccharides and a suitable quantity of beeswax and spun. If the medicament includes an oleaginous component, its concentration relative to the sucrose and beeswax should be considered in determining the delayed release pattern. The product can then be compacted readily into a pill or tablet form and administered orally along with a quantity of water sufficient to permit swallowing. With appropriate time delay, the medicament can be caused to release at a preselected point along the gastro-intestinal tract for most effective utilization by the body. Generally, only a small quantity of beeswax need be included and this, besides delaying the release, will aid pill or tablet formation.

To understand better the delayed release action, it should be remembered that the spun sugar products when containing a hydrophobic substance behave as colloids. A colloid is not known to be absorbed efficiently in the upper digestive tract and will normally pass into the intestines to be absorbed through the action of the bile and other juices. The beeswax delays the dispersal of the material long enough for it to be swallowed before it is released as a colloidal dispersion. A few additional examples might be helpful here.

EXAMPLE XVII

In this example the active ingredient is "DRAMAMINE" Liquid by Richardson-Vicks Inc. of Wilton, Conn. Each teaspoon is listed as containing 12.5 mg.

dimenhydrinate with cherry flavor, ethyl alcohol 5%, FD&C Red No. 40, glycerin, methylparaben, sucrose and water. 4 tsp. of "DRAMAMINE" Liquid was mixed with 1 tsp. of ground beeswax, 7 tsp. of sucrose, and ¼ tsp. of "Crisco" vegetable oil. The ingredients were mixed in a cup with a spoon and then spun producing a rich floss. Added to room temperature water, the floss floated. Added to water at 200° F., the floss dispersed immediately to form a colloidal-like dispersion. When placed in the mouth on the tongue, there was a brief hesitation of about 4 to 5 seconds, whereupon rapid dissolution occurred.

Some of the above floss was rolled between the fingers and easily formed into a firm ball. It is assumed that the beeswax under the heat and pressure from the fingers helped in compaction and binding of the floss. When this "pill" was placed in water at room temperature it took 15–20 minutes for the material to disperse. Initially it floated slightly below the water line, but after the delay formed a good colloidallike dispersion.

EXAMPLE XVIII

Bismuth Subsalicylate in powder form, obtained from Sigma Chemical Co. of St. Louis, Mo., was mixed in the ratio of 1 part bismuth subsalicylate to 4 parts "Natures Way" brand of liquid lecithin. The mixture was heated over a flame until the bismuth powder melted in the lecithin. ¼ cup of the resulting solution was added to ¾ cup sucrose and mixed for about 4 minutes with a spoon. Then 1 tsp. ground beeswax was added, and the composition was mixed for another 4 minutes. This blend of material was then spun producing an excellent floss. The floss was then subjected to the same tests as described in example XVII with essentially the same results, except the taste when placed in the mouth was not as pleasing as in example XVII due to the absence of flavoring agents other than that included in the sucrose.

EXAMPLE XIX

Next, ⅛ cup of "LIQUIPRIN" by Norcliff Thayer Inc. of Tarrytown, N.Y., (containing acetominophen 80 mg. per 1.86 ml., artificial raspberry and other flavors, citric acid, D&C Red 33, dextrose, FD&C Red 40, fructose, glycerin, methylparaben, polyethylene glycol, propylene glycol, propylparaben, sodium citrate, sodium gluconate, sucrose and water) was mixed with ½ cup sucrose, 1/16 cup "Crisco" vegetable oil, and 1 tsp. ground beeswax, and then spun to yield an excellent floss. It was then subjected to the same tests as described in example XVII with essentially the same results, the taste being excellent because of the separate flavoring agents.

To summarize, the addition of a small quantity of ground beeswax to the formulation in examples XVII, XVIII and XIX provides for a delayed release medicament, while facilitating compaction to form pills, tablets, suppositories or the like.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A method for preparing a pharmaceutical product having a predetermined release pattern comprising producing a mass of medicament bearing spun fibers by melt spinning a composition containing said medicament and at least one saccharide where the content of said composition has been selected such that said saccharide and medicament spin under conditions which do no deteriorate said medicament, and said mass of spun fibers when added to water at normal room temperature appears to be hydrophobic but disperses to form a colloidal or pseudo-colloidal dispersion when the temperature of said water is elevated sufficiently above normal room temperature.

2. A method for preparing a product according to claim 1, wherein said content of said composition has been selected with the ratio of said medicament to said saccharide exceeding the proportion that yields a mass of spun fibers which when placed in water at normal room temperature disperses rapidly therein.

3. A method for preparing a product according to claim 2, wherein said composition is the result of combining a medicament bearing vehicle with said saccharide where said vehicle includes petrolatum.

4. A method for preparing a product according to claim 1, wherein said composition includes an ingredient other than said medicament and said saccharide which stabilizes said mass of spun fibers causing said apparent hydrophobicity in water at normal room temperature while permitting said dispersion at said elevated temperature.

5. A method for preparing a product according to claim 4, wherein said ingredient is selected from the group consisting of beeswax and petroleum jelly.

6. A method of stabilizing spun saccharide which comprises in combination the steps of combining with at least one saccharide capable of being spun into fibers that are readily water-soluble a quantity of a substance selected from the group consisting of petrolatum, beeswax and combinations thereof, and thereafter processing said substance and saccharide combination to yield a mass of spun fibers.

7. A method according to claim 6, wherein sucrose is used as said saccharide.

8. A method according to claim 6, wherein glucose is used as said saccharide.

9. A pharmaceutic product comprising spun fibers of a spinnable, readily water-soluble material, an effective amount of a medicament, and an ingredient other than said medicament and said material which ingredient stabilizes said spun fibers and reduces the rate at which said spun fibers enter into a dispersed state when added to water.

10. A pharmaceutic product according to claim 9, wherein said ingredient is beeswax.

11. A pharmaceutic product according to claim 9, wherein said ingredient is petrolatum.

12. A pharmaceutic product according to claim 9, wherein said ingredient is selected from the group consisting of petrolatum, beeswax and combinations thereof.

13. A pharmaceutic product comprising a mass of spun fibers containing a saccharide and a dermatologically effective active ingredient where said mass of fibers when added to water at normal room temperature disperse at a slower rate than spun fibers of said saccharide alone.

14. A pharmaceutic product according to claim 13, wherein said spun fibers include a substance that slows without preventing dispersal of said mass of spun fibers in water at normal room temperature.

15. A pharmaceutic product according to claim 14, wherein said substance is selected from the group consisting of beeswax, petrolatum, and combinations thereof.

16. A pharmaceutic product according to claim 13, wherein said active ingredient is a petroleum jelly.

17. A pharmaceutic product according to claim 16, wherein said saccharide is selected from the group consisting of sucrose, lactose, glucose and combinations thereof.

18. A pharmaceutic product according to claim 17, wherein said saccharide is sucrose and said active ingredient is petroleum jelly with the ratio of petroleum jelly to sucrose exceeding 1:5 by volume.

19. A pharmaceutic product according to claim 13, wherein said active ingredient comprises an antibiotic constituent in combination with a petrolatum vehicle.

20. A pharmaceutic product according to claim 13, wherein said active ingredient comprises a corticoid constituent, and said spun fibers further include a quantity of petrolatum.

21. A pharmaceutic product according to claim 13, wherein said active ingredient is pectin.

22. A pharmaceutic product according to claim 21, wherein said spun fibers include a substance selected from the group consisting of beeswax, petrolatum, and combinations thereof.

23. A pharmaceutic product according to claim 22, wherein said substance is a petroleum jelly.

24. A pharmaceutic product according to claim 23, wherein said saccharide is selected from the group consisting of sucrose, lactose, glucose and combinations thereof.

25. A pharmaceutic product according to claim 24, wherein said saccharide is sucrose, said active ingredient is pectin, and said substance is petroleum jelly, with the ratio of the combined quantity of pectin and petroleum jelly to sucrose exceeding 1:5 by volume.

26. A product for consumption by introduction through the oral cavity where at least one of the ingredients of the product is noticeably unpalatable if introduced alone, said product comprising spun fibers of a spinnable, readily water-soluble material that is both palatable and able, when simultaneously present in the oral cavity with said unpalatable ingredient, to mask said unpalatableness, a quantity of an unpalatable ingredient having a slower rate of dissipation in the oral cavity than said readily soluble material when only the two are present, and a moderator substance for retarding solubilization of said readily soluble material to cause said readily soluble material to remain in the oral cavity at least as long as said unpalatable ingredient.

27. A product according to claim 26, wherein said readily water soluble material is a saccharide.

28. A product according to claim 27, wherein said unpalatable ingredient is a medicament.

29. A product according to claim 28, wherein said moderator is beeswax.

30. A product according to claim 29, wherein said medicament is essentially a combination of aluminum hydroxide and magnesium hydroxide.

31. A product according to claim 26, wherein said unpalatable ingredient is a medicament.

32. A product according to claim 31, wherein said moderator is beeswax.

33. A product according to claim 26, wherein said moderator is beeswax.

34. A pharmaceutic product comprising a mass of spun fibers containing a saccharide and a substance that slows without preventing dispersal of said mass of spun fibers in water at normal room temperature.

35. A pharmaceutic product according to claim 34, wherein said substance is selected from the group consisting of beeswax, petrolatum, and combinations thereof.

36. A pharmaceutic product according to claim 35, wherein said saccharide is selected from the group consisting of sucrose, lactose, glucose and combinations thereof.

37. A pharmaceutic product comprising spun fibers of a spinnable, readily water-soluble material, and an ingredient other than said material which ingredient stabilizes said spun fibers and reduces the rate at which said spun fibers enter into a dispersed state when added to water.

38. A pharmaceutic product according to claim 37, wherein said ingredient is beeswax.

39. A pharmaceutic product according to claim 37, wherein said ingredient is petrolatum.

40. A pharmaceutic product according to claim 37, wherein said ingredient is selected from the group consisting of petrolatum, beeswax and combinations thereof.

41. A pharmaceutic product comprising spun fibers of a spinnable, readily water-soluble material, an effective amount of a medicament, and an ingredient other than said medicament and said material which ingredient is from the group consisting of petrolatum, beeswax and combinations thereof.

42. A pharmaceutic product comprising spun fibers of a spinnable, readily water-soluble material, and an ingredient other than said material which ingredient is from the group consisting of petrolatum, beeswax and combinations thereof.

43. A stabilized spun saccharide comprising spun fibers of a spinnable, readily water-soluble saccharide and a substance other than said saccharide which substance by virtue of its presence stabilizes said spun fibers and reduces the rate at which said spun fibers enter into a dispersed state when in a quantity of water.

44. A stabilized spun saccharide according to claim 43, wherein said substance is selected from the group consisting of beeswax, petrolatum and combinations thereof.

45. A stabilized spun saccharide according to claim 44, wherein said petrolatum is essentially petroleum jelly.

46. A stabilized spun saccharide according to claim 45, wherein said saccharide is essentially sucrose.

47. A stabilized spun saccharide according to claim 44, wherein said saccharide is essentially sucrose.

48. A stabilized spun saccharide comprising spun fibers of a spinnable, readily water-soluble saccharide and a substance other than said saccharide which substance by virtue of its presence stabilizes said spun fibers and inhibits dissolution and dispersal of said fibers in an aqueous environment.

49. A stabilized spun saccharide according to claim 48, wherein said substance is selected from the group consisting of beeswax, petrolatum and combinations thereof.

50. A stabilized spun saccharide according to claim 49, wherein said petrolatum is essentially petroleum jelly.

51. A stabilized spun saccharide according to claim 50, wherein said saccharide is essentially sucrose.

* * * * *